US012635893B2

(12) United States Patent
Vanvinckenroye et al.

(10) Patent No.: US 12,635,893 B2
(45) Date of Patent: May 26, 2026

(54) PPG SIGNAL PROCESSING DEVICE AND CORRESPONDING COMPUTER-IMPLEMENTED METHOD

(71) Applicant: QOMPIUM, Hasselt (BE)

(72) Inventors: Amaury Vanvinckenroye, Sèvres (FR); Glenn De Witte, Herent (BE)

(73) Assignee: QOMPIUM, Hasselt (BE)

( * ) Notice: Subject to any disclaimer, the term of this patent is extended or adjusted under 35 U.S.C. 154(b) by 0 days.

(21) Appl. No.: 18/723,801

(22) PCT Filed: Dec. 22, 2022

(86) PCT No.: PCT/EP2022/087548
§ 371 (c)(1),
(2) Date: Jun. 24, 2024

(87) PCT Pub. No.: WO2023/118468
PCT Pub. Date: Jun. 29, 2023

(65) Prior Publication Data
US 2025/0000377 A1     Jan. 2, 2025

(30) Foreign Application Priority Data
Dec. 22, 2022     (EP) ..................................... 21216999

(51) Int. Cl.
*A61B 5/024*          (2006.01)
*A61B 5/00*           (2006.01)
(52) U.S. Cl.
CPC ...... *A61B 5/02405* (2013.01); *A61B 5/02416* (2013.01); *A61B 5/7278* (2013.01); *A61B 2503/40* (2013.01)
(58) Field of Classification Search
CPC .............. A61B 5/02405; A61B 5/7282; A61B 5/02416; A61B 5/7264
See application file for complete search history.

(56) References Cited

U.S. PATENT DOCUMENTS 5,243,980 A * 9/1993 Mehra .................... A61N 1/365
600/510
5,893,882 A * 4/1999 Peterson .............. A61N 1/3622
607/14
(Continued)

OTHER PUBLICATIONS

International Search Report dated Mar. 22, 2023.
Written Opinion dated Mar. 22, 2023.

*Primary Examiner* — Oommen Jacob
(74) *Attorney, Agent, or Firm* — IPSILON USA, LLP

(57) ABSTRACT

A photoplethysmography or PPG signal processing device configured to detect atrial flutter, includes a processor and memory including computer program code The processor and memory are configured to cause the PPG signal processing device to
obtain (101) at least one PPG signal (200) for a human or animal;
detect (102) heartbeats (201, 202, 203, 204, 205, . . . ) in the at least one PPG signal (200); and
determine (103) interbeat intervals (301, 302, 303, 304, . . . ) for pairs of consecutive heartbeats (201-202, 202-203, 203-204, 204-205, . . . ) in the at least one PPG signal (200).
The processor and memory cause the PPG signal processing device to detect (104) interbeat interval baselines, each interbeat interval baseline (302-304) corresponding to a plurality of consecutive interbeat intervals (302, 303, 304) that are constant within a predefined tolerance value;
determine (105) respective average interbeat interval values (401, 402, . . . ) for the interbeat interval baselines (302-304); and
detect (110) a relationship between the average interbeat interval values (401, 402, . . . ; 501, 502, . . . ).

10 Claims, 5 Drawing Sheets

(56) References Cited

U.S. PATENT DOCUMENTS

| | | | | | |
|---|---|---|---|---|---|
| 6,519,490 | B1 * | 2/2003 | Wiesel | .................. | A61B 5/361 |
| | | | | | 600/518 |
| 7,177,686 | B1 * | 2/2007 | Turcott | ............. | A61N 1/36585 |
| | | | | | 607/23 |
| 7,532,923 | B1 * | 5/2009 | Hayes-Gill | ......... | A61B 5/4362 |
| | | | | | 600/511 |
| 11,291,401 | B2 * | 4/2022 | Velo | ....................... | G06N 20/00 |
| 2005/0149125 | A1 * | 7/2005 | Kim | .................... | A61N 1/3925 |
| | | | | | 607/14 |
| 2008/0045851 | A1 * | 2/2008 | Cazares | ................ | A61B 5/363 |
| | | | | | 600/515 |
| 2014/0221845 | A1 | 8/2014 | Mestha | | |
| 2015/0112156 | A1 * | 4/2015 | He | .................... | A61B 5/02416 |
| | | | | | 600/483 |
| 2016/0045117 | A1 * | 2/2016 | Liu | ................... | A61B 5/02405 |
| | | | | | 600/502 |
| 2016/0249843 | A1 * | 9/2016 | Sugiyama | ........... | A61B 5/7264 |
| | | | | | 600/521 |
| 2020/0100693 | A1 | 4/2020 | Velo | | |
| 2025/0000377 | A1 * | 1/2025 | Vanvinckenroye | .. | A61B 5/7282 |

* cited by examiner

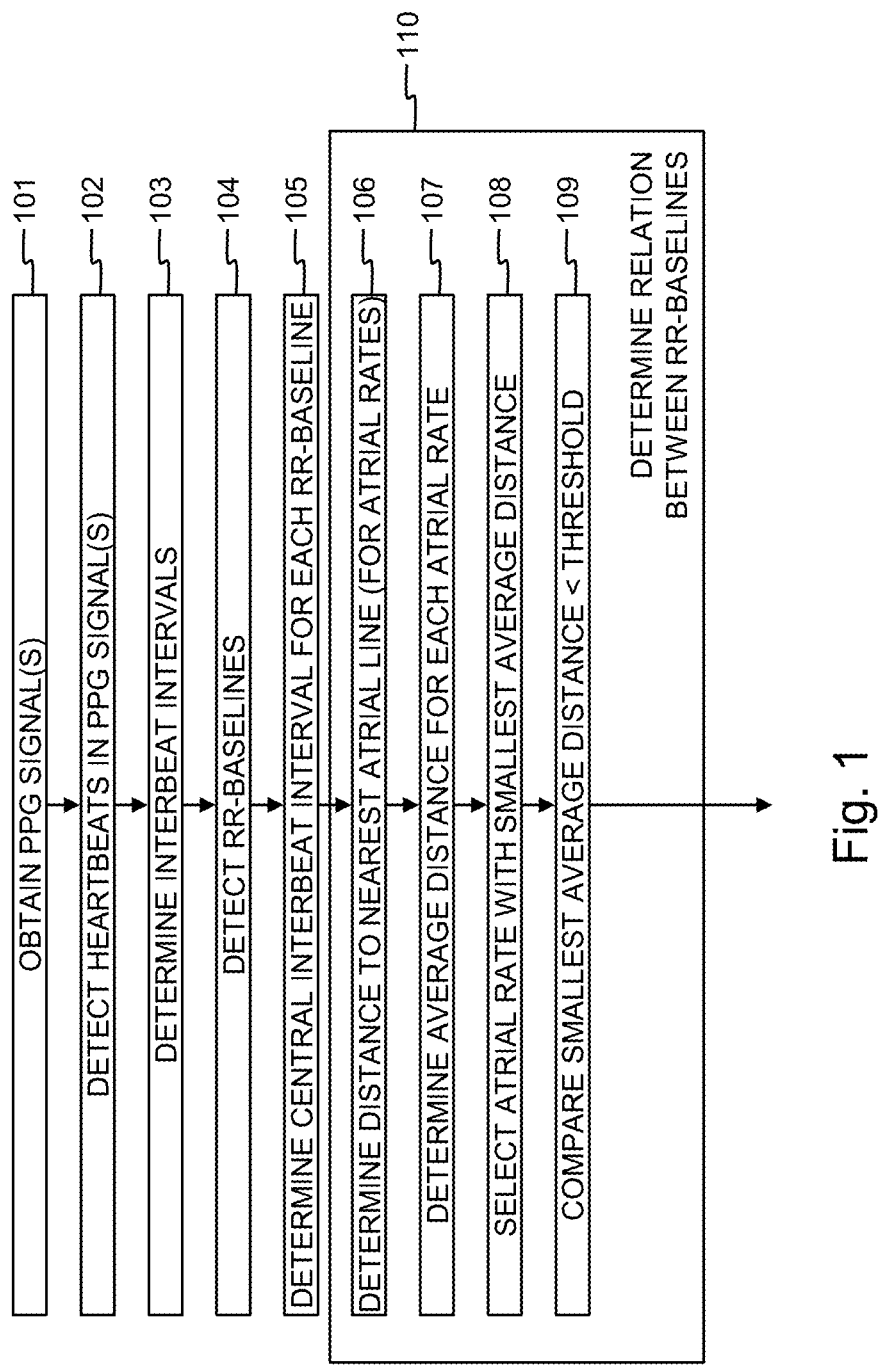

Fig. 1

OBTAIN PPG SIGNAL(S) 101

DETECT HEARTBEATS IN PPG SIGNAL(S) 102

DETERMINE INTERBEAT INTERVALS 103

DETECT RR-BASELINES 104

DETERMINE CENTRAL INTERBEAT INTERVAL FOR EACH RR-BASELINE 105

DETERMINE DISTANCE TO NEAREST ATRIAL LINE (FOR ATRIAL RATES) 106

DETERMINE AVERAGE DISTANCE FOR EACH ATRIAL RATE 107

SELECT ATRIAL RATE WITH SMALLEST AVERAGE DISTANCE 108

COMPARE SMALLEST AVERAGE DISTANCE < THRESHOLD 109

DETERMINE RELATION BETWEEN RR-BASELINES 110

PPG SIGNAL PROCESSING DEVICE AND CORRESPONDING COMPUTER-IMPLEMENTED METHOD

RELATED APPLICATION

This application is a National Phase of PCT/EP2022/087548 filed on Dec. 22, 2022, which claims the benefit of priority from European Patent Application No. 21 216 999.9 filed on Dec. 22, 2021, the entirety of which are incorporated by reference.

FIELD OF THE INVENTION

The present invention generally relates to photoplethysmography or PPG, an optical technique to detect blood volume changes that enables to monitor various physiological parameters. The invention in particular concerns the processing of one or more PPG signals obtained for a human or animal in order to facilitate the detection of a wider variety of heart rhythm problems.

BACKGROUND OF THE INVENTION

Photoplethysmography (PPG) is an optical technique that allows to monitor one or more physiological parameters by detecting blood-volume changes in the peripheral circulation. PPG makes use of light absorption by blood to track these volumetric changes. When a light source illuminates the skin, the reflected light varies as blood flows. A light sensor then converts these variations in light reflection into a digital signal, the so-called PPG signal. PPG signals are typically recorded using a pulse oximeter or photodetector, for instance the camera integrated in an electronic device like a person's smartphone, smartwatch or other smart wearable or non-wearable device.

A distinction is made between remote PPG and contact PPG. Remote PPG is non-obtrusive for the monitored person but poses major challenges to signal detection and signal processing. As a consequence, the use of remote PPG remains limited to everyday applications like leisure or fitness as its accuracy and reliability are insufficient for medical applications. Contact PPG, wherein the measurement components are in direct contact with the skin, results in a more reliable, more accurate PPG signal that facilitates medical diagnosis.

PPG can be used, among other applications, to monitor cardiovascular and hemodynamic parameters such as heart rate, heart rate variability, blood pressure, or to monitor other physiological variables such as stress, respiration or autonomic functions. One key part of an accurate monitoring with PPG is to obtain a high-quality, artefact-free signal, as PPG can be affected by various sources of noise. Methods for accurate and reliable PPG measurement are described for instance in European patent application EP3449820A1 from applicant Qompium, entitled "Computer-Implemented Method and System for Direct Photoplethysmography (PPG)", and in European patent application EP3473173 from applicant Qompium, entitled "Computer-Implemented Method and System for Direct Photoplethysmography (PPG) with Multiple Sensors".

In a medical context, contact PPG is mainly used for atrial fibrillation (AF) risk detection, the most common cardiac rhythm disorder. Other cardiac rhythm disorders are typically detected via an electrocardiogram (ECG) obtained for instance by a Holter monitoring system.

It is desirable to use PPG signals that are easily obtainable through wearables to detect other abnormal heart rhythms like for instance tachycardia or atrial flutter. Atrial flutter is a type of abnormal heart rhythm caused by an abnormal electrical circuit in the upper chamber of the heart, named the atria, that makes the atria beat quickly. In a normal functioning heart, electrical pulses are sent from the sinus node—the so-called SA node—in the right atrium of the heart. This way, this node controls the heart rate and timing of heartbeats. In case of atrial flutter, an abnormal electrical circuit is formed in the atria. This abnormal electrical circuit takes over the heart rhythm and rate, and causes abnormally frequent contractions in the upper chambers.

Atrial flutter also may cause the lower chambers of the heart—the so-called ventricles—to beat faster but often not as fast as the atria. In a normal functioning heart, the atrial rate or AR equals the ventricular rate or VR. In case of atrial flutter, the ventricular rate typically is an integer fraction of the atrial rate, with the ratio between the AR and VR, the so-called AV conduction rate, being equal to 2:1, 3:1 or 4:1. The AV conduction rate may be constant. In an example where the AV conduction rate remains 3:1 while the AR is 300 bpm (beats per minute), the VR will be 100 bpm. The AV conduction rate may also be alternating. In an example where the AV conduction ratio is alternating between the 2:1, 3:1 and 4:1 ratios while the AR is 300 bpm, the VR is alternating between 150 bpm, 100 bpm and 75 bpm.

On a PPG signal, the ventricular rate can be seen but the atrial rate cannot be seen. Consequently, the presence of flutter waves typically cannot be seen on a photoplethysmogram or PPG signal plot. Reliable atrial flutter detection therefore requires confirmation through an electrocardiogram or ECG.

The article "Detecting Atrial Fibrillation and Atrial Flutter in Daily Life Using Photoplethysmography Data" from the authors Eeriksinen L. M. et al., published in IEEE J Biomed Health Inform, 2020 June, 1610-1618, pretends to describe a way to detect atrial flutter using PPG. However, the features extracted from the PPG signal by Eeriksinen et al. are not particular for atrial flutter detection. Classical heart rate variability features such as entropy, RMSSD, pNN70, etc., are used, which are traditional features found in the literature. If these features would allow to reliably detect atrial flutter, this would have been confirmed in medical literature. The study underlying the article contains only 5 atrial flutter patients, 3 of which are used for training the classifier, leaving 2 patients in the test set. This gives limited insights into the performance as the limited patient size probably biases the results. Moreover, it is noticed that Eeriksinen et al. perform classification on individual 30-second strips of a PPG signal, not at the patient-level.

According to the state of the art on PPG, atrial flutter is often mentioned within a long list of arrhythmia that can be detected, but existing literature fails to describe how PPG signals must be processed to detect atrial flutter and distinguish atrial flutter from other arrhythmia.

United States patent application US2020/0100693A1 entitled "Arrhythmia Monitoring Using Photoplethysmography" describes atrial flutter" in [0070] with reference to the atrial rate and ventricular rate. In [0076] in D14 seems to teach that the average RR-interval can be used as parameter to detect tachycardias such as atrial flutter, but the document fails to teach how such RR-intervals must be processed in order to be able to detect atrial flutter.

United States patent application US2021/0007621A1 entitled "Method to Analyse Cardiac Rhythms Using Beat-To-Beat Display Plots" suggests in paragraphs [0068],

[0074], [0105] and in FIG. 10 that atrial flutter can be detected from beat-to-beat display plots, but also this document contains no guidance towards preferred processing of PPG signals in order to be able to reliably detect and discriminate atrial flutter from other heart rhythm diseases.

United States patent application US2017/0032221A1 entitled "Method, Electronic Apparatus and Computer Readable Medium of Constructing Classifier for Disease Detection" refers in [0004] and FIG. 1C to a classifier for atrial flutter but relies on features of an ECG signal: disappearance of the interval between the end of the T-wave and the beginning of the P-wave.

In United States patent application US2016/0302677A1 entitled "Calibrating for Blood Pressure Using Height Difference", paragraphs [0126], [0130] and FIG. 16B suggest to detect atrial flutter by looking for normal (or regular) heart rates and for changes in heart rate that are multiples of each other, detectable through clusters offset from the diagonal in a plot shown in FIG. 16B where $RR_{i+1}$ is plot vs. $RR_i$.

United States patent application US2014/0221845A1 describes in paragraphs [0036]-[0038] obtaining a PPG signal and filtering the PPG signal to detect peaks (heartbeats) therein. US2014/0221845A1 further describes determining peak-to-peak intervals (RR-intervals). From the RR-intervals, heartrate dynamics are established, useful to detect arrhythmia. US2014/0221845A1 however does not describe a technique to detect atrial flutter.

It is an objective of the present invention to provide an improved technique to process PPG signals in order to extract information from PPG signals that is useful to detect atrial flutter or other abnormal heart rhythms which are nowadays difficult to detect or discriminate reliably based on PPG signals.

SUMMARY OF THE INVENTION

According to embodiments of the invention, the above-defined objective is realized by a photoplethysmography signal processing device as defined by claim 1, abbreviated as PPG signal processing device, configured to detect atrial flutter, the PPG signal processing device comprising at least one processor and at least one memory including computer program code, the at least one memory and the computer program code configured to, with the at least one processor, cause the PPG signal processing device to:

obtain at least one photoplethysmography signal, abbreviated as PPG signal, for a human or animal;

detect heartbeats in the at least one PPG signal;

determine interbeat intervals for pairs of consecutive heartbeats in the at least one PPG signal;

detect interbeat interval baselines, each interbeat interval baseline corresponding to a plurality of consecutive interbeat intervals that are constant within a predefined tolerance value;

determine respective average interbeat interval values for respective ones of the interbeat interval baselines; and detect a relationship between the average interbeat interval values and thereto:

determine respective distances between the average interbeat interval values of the interbeat interval baselines and nearest atrial lines for a subset of atrial rates, wherein the subset of atrial rates comprises integer beat per minute values between a lower bound and an upper bound and wherein atrial lines correspond to integer parts of the atrial rates;

determine for each atrial rate in the subset of atrial rates an average distance between the average interbeat interval values and nearest atrial lines for the atrial rate;

select the atrial rate for which said average interbeat interval values have the smallest average distance to the atrial lines; and detect atrial flutter if the smallest average distance is smaller than a predetermined threshold distance.

Indeed, the existence of a relationship and/or the nature of the relationship between central or averaged interbeat values for baselines (also named RR-baselines) detected based on PPG signal(s) for a single person or animal, may allow to reliably detect certain arrhythmia like for instance alternating atrial flutter. Other heart arrhythmias that could be detected this way are for instance atrioventricular nodal reentry tachycardia (AVNRT), atrioventricular reciprocating tachycardia (AVRT), atrial tachycardia, multifocal atrial tachycardia. These arrhythmias are part of the category of supraventricular tachycardia, where also atrial flutter belongs to, as explained above.

According to embodiments of the invention, one or more PPG signals are obtained for a single person or animal. In these PPG signals, heartbeats are detected using state-of-the-art algorithms that determine peaks in the PPG signals that correspond to heartbeats of the person or animal and that determine the timing of such peaks. Thereafter, interbeat intervals, also named RR-intervals or peak-to-peak intervals, are determined. This implies that for each pair of consecutive heartbeats in the PPG signal(s), the time interval between these heartbeats is determined. Instead of looking for variation in the heart rate in order to detect a heart rate variability indicative for a heart arrhythmia, the PPG processing device according to the invention then looks for interbeat interval baselines, which are short periods of time wherein the interbeat interval or heart rate remains substantially constant, i.e. constant within a predefined tolerance value for the heart rate variability in an interbeat interval baseline. Hence, all consecutive interbeat intervals that are equal within the set tolerance value together form part of a single interbeat interval baseline. According to the invention, multiple interbeat interval baselines are detected for a single person or animal, across one or plural PPG signals obtained for that person or animal. These different interbeat interval baselines shall typically have different lengths but each interbeat interval baseline must comprise a plurality of subsequent interbeat intervals that are substantially equal. It is possible that a minimum length is set for interbeat interval baselines, corresponding to a minimum amount of subsequent interbeat intervals that must be constant in order to be considered an interbeat interval baseline. Within each interbeat interval baseline, the interbeat interval is averaged, thus obtaining an average value or central value for the time in between consecutive heartbeats for each detected period wherein the heart rate remains substantially constant. Thereupon, the existence of a relationship between these averaged interbeat intervals is searched for and outputted. The averaged interbeat intervals may for instance be equal (within tolerances), the averaged interbeat values may be integer multiples of a lowest value (within tolerances), the averaged interbeat values may be integer parts of a common multiple value (within tolerances), etc.

The present invention brings the advantage that certain arrhythmias, in particular arrhythmias that are part of the category of supraventricular tachycardia, can be detected reliably from PPG signals that are collected at multiple occurrences across time for a same patient, person or animal, using convenient wearables equipped with a photodetector.

In order to establish the presence of a relationship between the central interbeat interval values determined for different interbeat interval baselines of a single person or animal, these central interbeat interval values may be compared to atrial lines. The atrial lines correspond to integer parts of a common multiple value, and the common multiple value represents an atrial rate or AR value. For a single AR value, for instance 180 bpm, the first three atrial lines correspond to 0.67 seconds (or 90 bpm, being ½ of the AR), 1.00 seconds (or 60 bpm, being ⅓ of the AR), and 1.33 seconds (or 45 bpm, being ¼ of the AR). For each central interbeat interval value, it is determined which of the atrial lines (0.67 seconds, 1.00 seconds or, 1.33 seconds) is the nearest, and the distance to the nearest atrial line is determined. This is then repeated for a subset of atrial rates, for instance 180 bpm, 182 bpm, 184 bpm, . . . , 300 bpm. A small distance between the central interbeat intervals and atrial lines of a single AR indicates that the detected interbeat interval baselines (periods wherein the interval between subsequent heartbeats or heat rate remains substantially constant) all occur when the person's atria beats at a particular rate.

In order to establish if the interbeat interval baselines detected for a single person or animal occur when the person's or animal's atria beats at a particular rate (the AR), the distances measured between the respective central interbeat intervals and the nearest atrial line for that AR are averaged. This way, a single value is obtained representing across all PPG signals the distance between the baseline interbeat intervals of a person during short periods with constant interbeat interval and the respective nearest atrial lines for a single AR. Such single value can be determined for each AR value in the subset of considered AR values.

Out of the subset of atrial rates for which the central interbeat interval values in interbeat interval baselines are compared to the atrial lines, the atrial rate is selected for which the average distance of the interbeat interval baselines to the atrial lines is the smallest. If interbeat interval baselines occur at a particular AR, the so selected atrial rate is the best candidate for the particular AR.

The PPG signal processing device may be used to detect heart arrhythmias that are part of the category of supraventricular tachycardia like atrial flutter, atrioventricular nodal reentry tachycardia (AVNRT), atrioventricular reciprocating tachycardia (AVRT), atrial tachycardia, multifocal atrial tachycardia. Embodiments of the invention may comprise a single classifier for a single arrhythmia or may comprise plural classifiers to detect plural arrhythmias. The smallest average distance between the interbeat interval during interbeat interval baselines and atrial lines for a subset of atrial rates may serve as input parameter for a classifier that determines if the person or animal suffers from atrial flutter.

A simple-to-implement atrial flutter classifier may compare the obtained smallest average distance (between the interbeat interval during interbeat interval baselines and closest atrial lines for a subset of atrial rates) to a predetermined distance threshold value. When the smallest average distance stays below this predetermined distance threshold value, an atrial rate is found for which the interbeat interval during different interbeat interval baselines approaches the atrial lines very closely. The interbeat interval baselines in other words very likely occur when the atria is beating at a particular atrial rate. The interbeat intervals in different interbeat interval baselines may differ substantially but they all closely match one of the atrial lines of that particular atrial rate. This is an indication for atrial flutter and the classifier may therefore reliably classify the person or animal as an atrial flutter patient.

It is noticed that the threshold-based classifier could be used on its own, meaning that the average distance to the closest set of atrial lines can be compared to some threshold to classify a person/animal as atrial flutter patient. If the average distance value is below the threshold, it's atrial flutter. If the average distance value is above the threshold, it's not atrial flutter. The threshold-based classifier can also be used in combination with other methods to extract information from the PPG recordings. The current method then serves to calculate a feature, the feature being the average distance to the closest set of atrial lines. This feature, along with other features computed by other methods, can then be used to train a classifier (a decision tree, a support vector machine, a k-nearest neighbour, a neural network, etc.) for one or several arrhythmias. As an example, one could determine:

the average distance to the closest set of atrial lines;

the average heart rate;

the standard deviation of RR intervals;

the mean amplitude of PPG heartbeats;

the standard deviation of amplitude of PPG heartbeats;

. . . .

and use a subset or all of these features to train a classifier. Generally speaking, the invention contributes to providing a way to calculate a feature for heart rhythm variability.

In embodiments of the PPG signal processing device according to the invention, as defined by claim 2, the average distance corresponds to a weighted square distance wherein the length or duration of an interbeat interval baseline serves as respective weight for the square distance between the interbeat interval baseline and a nearest atrial line in the average distance.

Whereas the average distance between the central interbeat interval values of interbeat interval baselines and the respective nearest atrial lines of an atrial rate may be determined as the mean value, the median value, the modus value, etc., preferred embodiments of the invention determine the average distance as a weighted square distance value. In the weighted square distance value, each distance between the central interbeat interval value of an interbeat interval baseline and the corresponding nearest atrial line is squared and weighted with a respective weight value that is proportional to the length or duration of the interbeat interval baseline. This way, the distance value determined for a longer interbeat interval baseline gets a weight or importance in the overall average distance that is higher than the weight or importance assigned to the distance value determined for a shorter interbeat interval baseline. Weighting the distances to the nearest atrial lines using the length of interbeat interval baselines improves the reliability of the PPG signal processing device and the disease classification based thereon.

In embodiments of the PPG signal processing device according to the invention, as defined by claim 3, the atrial lines for an atrial rate out of the subset of atrial rates correspond to half of the atrial rate, a third of the atrial rate, and a fourth of the atrial rate.

Indeed, in case of alternating atrial flutter, it may be assumed that the interbeat intervals of RR-baselines fall on lines that are integer fractions of a base atrial rate, with the AV conduction ratio being equal to 2:1, 3:1 or 4:1. It is therefore sufficient to consider for each atrial rate in the subset the atrial lines that correspond to half, a third or a fourth of the atrial rate.

In embodiments of the PPG signal processing device according to the invention, as defined by claim 4, the subset of atrial rates comprises all integer rates between a lower bound and an upper bound, preferably between 180 beats per minute and 400 beats per minute.

Thus, in order to determine the atrial rate for which the interbeat intervals of RR-baselines approach the atrial lines most closely, a limited subset of atrial rates may be considered. This limited subset may contain for instance all integer values between a lowest atrial rate and a highest atrial rate. The lowest atrial rate may for instance be chosen equal to 180 bpm. The highest atrial rate may for instance be chosen equal to 400 bpm. In alternative implementations, the lowest atrial rate and/or the highest atrial rate may be chosen differently, and instead of each integer value a step value may be configured corresponding to the step or distance between two successive atrial rates considered.

In embodiments of the PPG signal processing device according to the invention, as defined by claim 5, the average interbeat interval value for an interbeat interval baseline corresponds to one of the following:

the mean value of interbeat interval values that belong to the interbeat interval baseline;

the median value of interbeat interval values that belong to the interbeat interval baseline;

the modus value of interbeat interval values that belong to the interbeat interval baseline; or the mid-range value of interbeat interval values that belong to the interbeat interval baseline.

Embodiments of the invention determine, as explained above, an average value or central value for the interbeat interval in each RR-baseline. As the interbeat interval remains substantially constant within an RR-baseline, the interbeat values are assumed to be equal or nearly equal. Still it makes sense to determine an average or central value for the continued processing, e.g. comparison of such average or central value to atrial lines of atrial rates. The average or central value may be chosen to be less sensitive for outliers, like for instance the median value or modus value. Alternatively, since outliers may be absent as a result of the variability tolerance, the average or central value may also be determined using the mean value or the mid-range value.

Embodiments of the PPG signal processing device according to the invention, as defined by claim 6, further comprise means to configure a minimum amount for the plurality of consecutive interbeat intervals that forms an interbeat interval baseline.

Allowing the user to configure the minimum amount of interbeat intervals that constitutes an RR-baseline, provides the user a parameter to control the accuracy and reliability of the device. When the minimum length of RR-baselines is set higher, the accuracy will increase as the risk for considering a short period of time wherein the heart rate incidentally remains constant as an RR-baseline indicative for certain heart rhythm diseases is reduced this way.

Embodiments of the PPG signal processing device according to the invention, as defined by claim 7, further comprise means to configure said predefined tolerance value.

Indeed, the variability tolerance constitutes a second parameter allowing the user to control the accuracy and reliability of the device, when made configurable. A smaller variability tolerance value will result in fewer periods of time with substantially constant interbeat interval being considered as RR-baselines (due to a value outside the variability tolerance, a period of time may not reach the minimum required length to be considered an RR-baseline).

Further, within RR-baselines, the interbeat interval values will in general be closer to each other (they can differ no more than the variability tolerance). The risk for considering a short period of time wherein the heart rate incidentally remains constant as an RR-baseline indicative for certain heart rhythm diseases is thus reduced when the variability tolerance is decreased, or vice-versa.

In addition to a PPG signal processing device, the present invention also concerns, as defined by claim 8, a corresponding computer-implemented method for processing a photoplethysmography signal, abbreviated as PPG signal, to detect atrial flutter, the method comprising:

obtaining at least one photoplethysmography signal, abbreviated as PPG signal, for a human or animal;

detecting heartbeats in the at least one PPG signal;

determining interbeat intervals for pairs of consecutive heartbeats in the at least one PPG signal;

detecting interbeat interval baselines, each interbeat interval baseline corresponding to a plurality of consecutive interbeat intervals that are constant within a predefined tolerance value;

determining respective average interbeat interval values for respective ones of the interbeat interval baselines; and detecting a relationship between the average interbeat interval values and thereto:

determining respective distances between the average interbeat interval values of the interbeat interval baselines and nearest atrial lines for a subset of atrial rates, wherein the subset of atrial rates comprises integer beat per minute values between a lower bound and an upper bound and wherein atrial lines correspond to integer parts of the atrial rate;

determining for each atrial rate in the subset of atrial rates an average distance between the average interbeat interval values and nearest atrial lines for the atrial rate;

selecting the atrial rate for which the average interbeat interval values have the smallest average distance to the atrial lines; and detecting atrial flutter if the smallest average distance is smaller than a predetermined threshold distance.

According to a further aspect, the present invention also concerns a computer program product as defined by claim 9, comprising computer-executable instructions for performing the method according to the invention when the program is run on a computer.

According to yet another aspect, the present invention concerns a computer readable storage medium as defined by claim 10, comprising the computer program product according to the invention.

BRIEF DESCRIPTION OF THE DRAWINGS

FIG. 1 illustrates the sequence of steps executed by an example embodiment of the PPG processing device according to the present invention;

DETAILED DESCRIPTION OF EMBODIMENT(S)

FIG. 1-5 illustrate an embodiment of the PPG processing device that is configured to detect RR-baselines and compare such RR-baselines with atrial lines corresponding to atrial rates in order to detect atrial flutter.

Figures 2, 3:
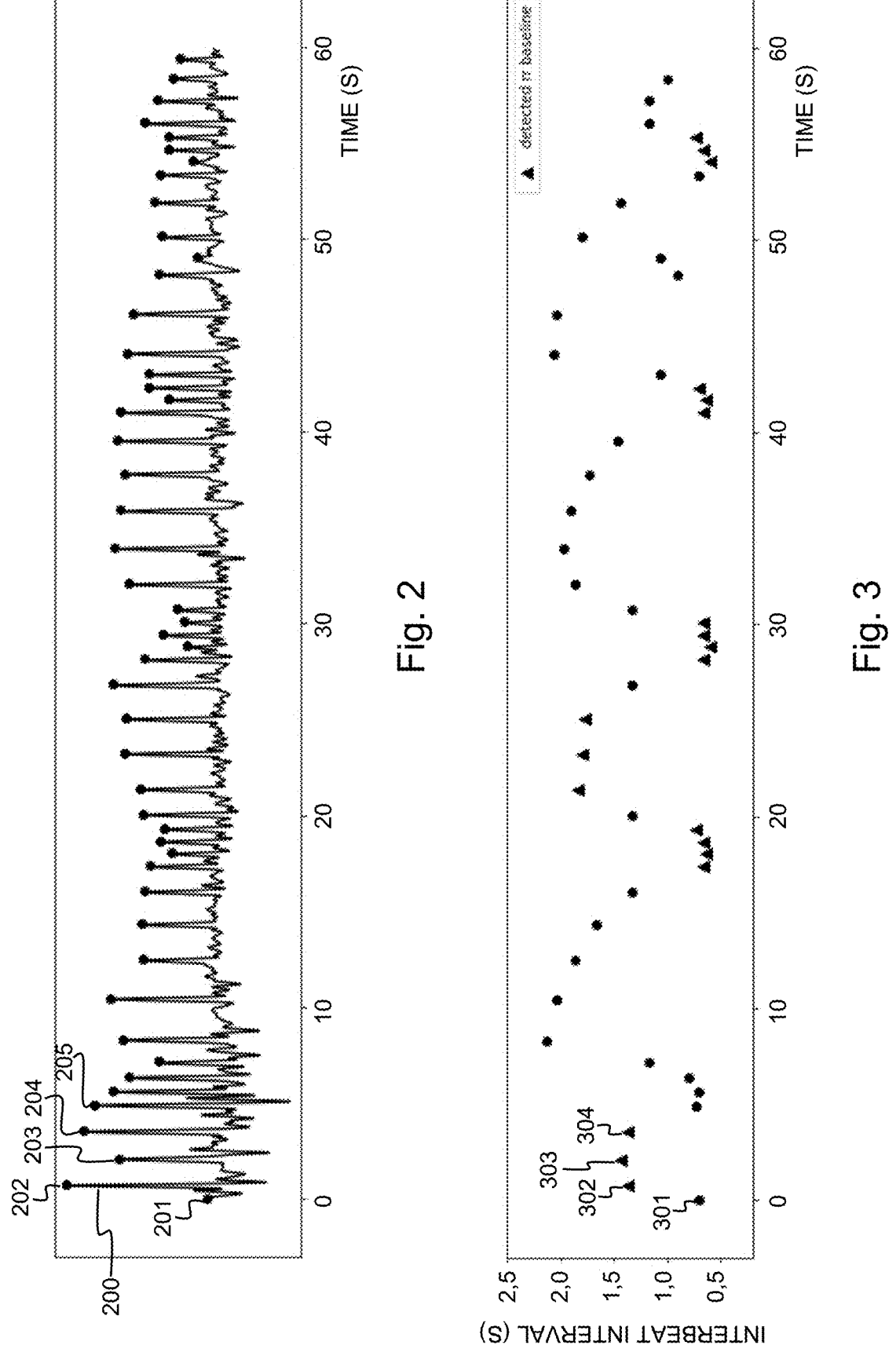
FIG. 2 illustrates the step of detecting heartbeats in a PPG signal 200 as performed by an example embodiment of the PPG processing device according to the present invention.
FIG. 3 illustrates the steps of determining interbeat intervals and determining RR-baselines based on the PPG signal 200 of FIG. 2, as performed by an example embodiment of the PPG processing device according to the present invention.

In a first step, denoted 101, the PPG processing device obtains one or plural PPG signals for a person. FIG. 2 shows a PPG signal 200 spanning 60 seconds that is obtained for a person in step 101.

In a second step, denoted 102, the PPG processing device detects heartbeats in the PPG signal. In FIG. 2, the dots 201, 202, 203, 204, 205, etc., represent heartbeats that are detected in the PPG signal 200. These heartbeats are detected through state-of-the-art peak detection algorithms applied to PPG signal 200 or to portions of PPG signal 200.

In a third step, denoted by 103, the PPG processing device determines the length of interbeat intervals for pairs of consecutive heartbeats in the PPG signal. These interbeat intervals may be outputted or plotted in a tachogram like the one shown in FIG. 3. In FIG. 3, dot 301 represents the interbeat interval between the first heartbeat 201 and the second heartbeat 202 detected in the PPG signal 202. The interbeat interval corresponds to the time lapsed in between the heartbeats 201 and 202, and is expressed in seconds. From FIG. 3, it is seen that the interbeat interval 301 between heartbeat 201 and heartbeat 202 corresponds to 0.7 seconds. Similarly, the triangle 302 represents the interbeat interval between the second heartbeat 202 and the third heartbeat 203 detected in PPG signal 202. This second interbeat interval 302 corresponds to 1.40 seconds. Further, triangle 303 represents the interbeat interval between the third heartbeat 203 and the fourth heartbeat 204 detected in PPG signal 202. This third interbeat interval 303 corresponds to 1.45 seconds. Triangle 304 in FIG. 3 represents the interbeat interval between the fourth heartbeat 204 and the fifth heartbeat 205 detected in PPG signal 202. This fourth interbeat interval 304 corresponds to 1.42 seconds. Each subsequent dot or triangle in FIG. 3 corresponds to an interbeat interval between a pair of consecutive heartbeats detected in the PPG signal 200. When plotted on a timeline, as is done in FIG. 3, these interbeat intervals constitute a tachogram.

In a fourth step, denoted 104 in FIG. 1, the PPG processing device determines RR-baselines. An RR-baseline corresponds to a plurality of consecutive interbeat intervals that are equal (within a variability tolerance). In FIG. 3, the detected RR-baselines are represented by triangles. Interbeat intervals that are not part of an RR-baseline are represented by dots. The interbeat intervals 302, 303 and 304 for example constitute a first RR-baseline, because they are consecutive interbeat intervals and their respective values vary less than 0.05 seconds (which is assumed to be the variability tolerance in FIG. 3). In addition to the RR-baseline formed by the interbeat intervals 302, 303 and 304, FIG. 3 shows five additional RR-baselines detected based on PPG signal 200. Two parameters define the accuracy of the RR-baseline detection step: the minimum length of an RR-baseline (set at 3 interbeat intervals in FIG. 3) and the variability allowed within an RR-baseline (set at 0.05 seconds in FIG. 3). Increasing the minimum length of an RR-baseline and/or decreasing the variability tolerance shall improve the accuracy and reliability of the PPG processing device as these parameter modifications will result in less time intervals wherein the heart rate accidentally remains constant being considered as RR-baselines (less false positives).

In a fifth step, denoted 105 in FIG. 1, the PPG processing device determines a central interbeat interval value for each RR-baseline detected in step 104. The central value or average value may for instance correspond to the mean value of all interbeat interval values of the RR-baseline. Alternatively, the median value, the modus value, the mid-range value, or another central value may be considered. In the example of FIG. 3, the mean value is determined as the central value for the interbeat values of an RR-baseline. For the RR-baseline that contains the interbeat intervals 302, 303, 304, this central value hence corresponds to (1.40+ 1.45+1.42)/3=1.42 seconds. Similarly, the central baseline value is determined for each of the detected RR-baselines. These central baseline values, obtained for a single person across one or plural PPG signals, may then be plotted against an index, as is done in FIG. 4 and FIG. 5.

Depending on the arrhythmia or arrhythmias looked after, the central RR-baseline values are then analysed in order to establish if certain relationships exist. This is indicated by 110 in FIG. 1. In an example where atrial flutter is looked after, the PPG processing device may for instance be configured to detect if the central RR-baseline values substantially correspond to alternating integer parts (atrial lines) of a common multiple value (atrial rate), where the alternating integer parts either represent half, a third or a fourth of the common multiple value. The existence of other relationships between the central RR-baseline values may be investigated if other arrhythmias are to be detected by the PPG signal processing device.

Figure 4:
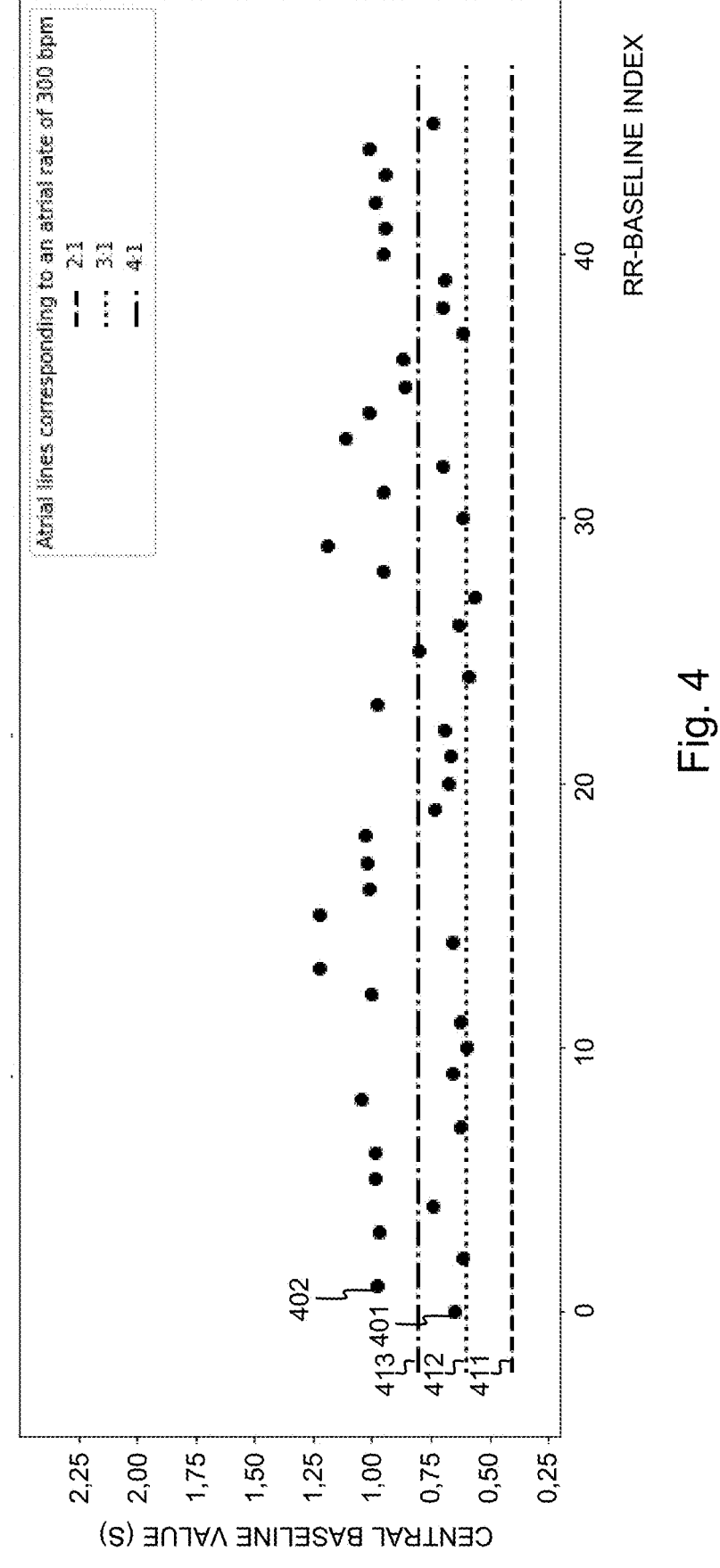
FIG. 4 illustrates the steps of determining central interbeat intervals for the RR-baselines as detected in FIG. 3 and comparing the RR-baselines with atrial lines for an atrial rate of 300 bpm, as performed by an example embodiment of the PPG processing device according to the present invention.

In order to compare the RR-baselines with atrial lines the distance between the central interbeat value of a detected RR-baseline and the respective atrial lines corresponding to an atrial rate is determined, and the nearest distance is maintained. This is illustrated by FIG. 4 wherein 401 represents the central interbeat value of a first RR-baseline, 402 represents the central interbeat value of a second RR-baseline, etc. In FIG. 4, the atrial rate of 300 bpm is considered and the three atrial lines corresponding to this rate are represented by dashed line 411 (half of the atrial rate corresponds to 150 bpm or 0.40 seconds interbeat interval), dotted line 412 (a third of the atrial rate corresponds to 100 bpm or 0.60 seconds interbeat interval), and dash-dotted line 413 (a fourth of the atrial rate corresponds to 75 bpm or 0.80 seconds interbeat interval). For the first RR-baseline, the nearest atrial line to central interbeat interval value 401 is line 412, so the distance between central interbeat interval value 401 and atrial line 412 is maintained. For the second RR-baseline, the nearest atrial line to central interbeat interval value 402 is line 413, so the distance between central interbeat interval value 402 and atrial line 413 is maintained. Similarly, the distance between each central interbeat interval value, represented by a dot in FIG. 4, and the atrial lines 411, 412, 413 is determined, and the smallest distance, i.e.

the distance to the nearest atrial line, is maintained. In step 106 of FIG. 1, this process, which is illustrated in FIG. 4 for the atrial rate of 300 bpm, is repeated for a subset of atrial rates, for example all integer atrial rate values between 180 bpm and 400 bpm.

Figure 5:
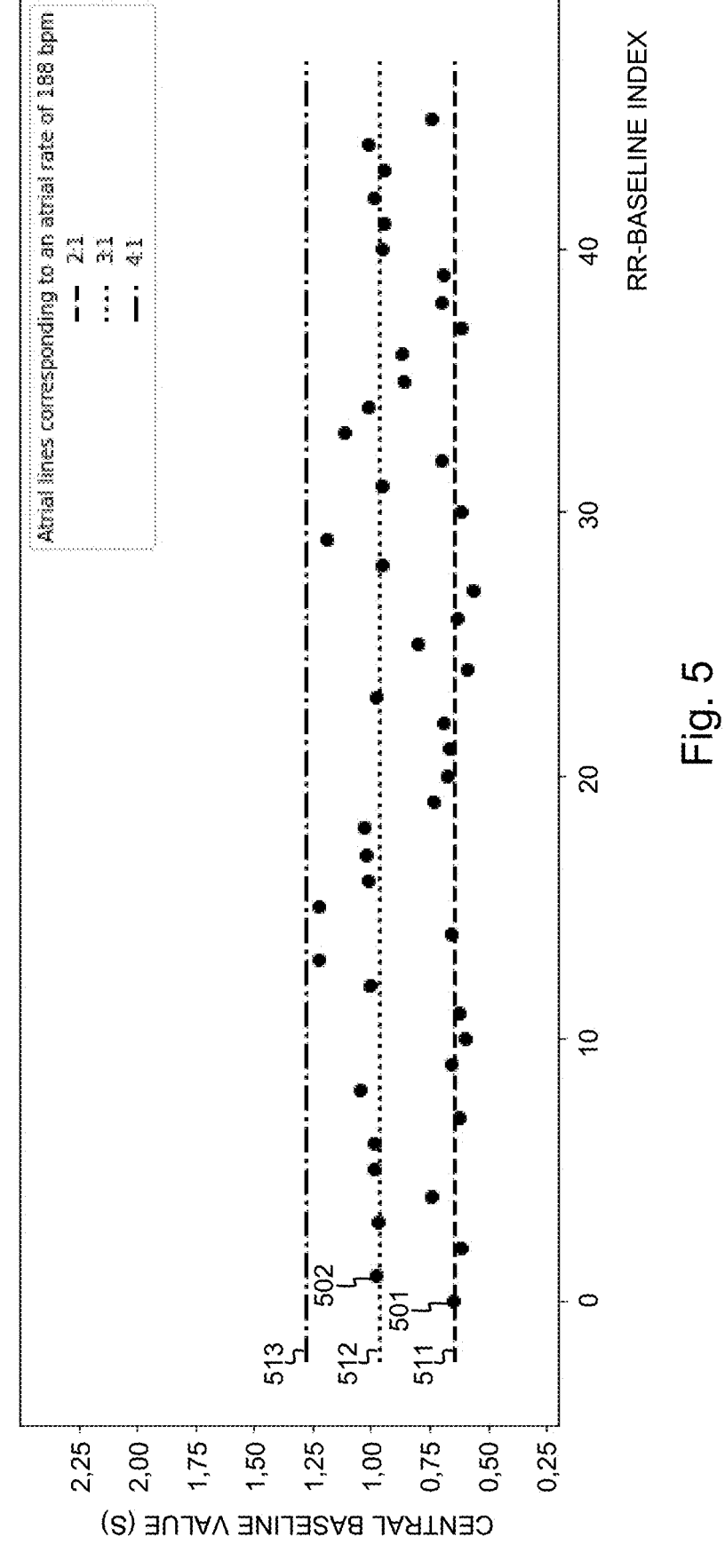
FIG. 5 illustrates the step of selecting an atrial rate whose atrial lines have the smallest average distance to the central RR-baseline values, as performed by an example embodiment of the PPG processing device according to the present invention.

FIG. 5 for instance illustrates the above-described distance determination to atrial lines corresponding to the atrial rate of 188 bpm. The dots in FIG. 5 representing the central interbeat interval values of respective RR-baselines correspond to the dots in FIG. 4. This, interbeat interval value 501 corresponds to interbeat interval value 401, interbeat interval value 502 corresponds to interbeat interval value 402, and so on. The three atrial lines corresponding to atrial rate of 188 bpm are represented by dashed line 511 (half of the atrial rate corresponds to 94 bpm or 0.64 seconds interbeat interval), dotted line 512 (a third of the atrial rate corresponds to 62.7 bpm or 0.96 seconds interbeat interval), and dash-dotted line 513 (a fourth of the atrial rate corresponds to 47 bpm or 1.28 seconds interbeat interval). For the first RR-baseline, the nearest atrial line to central interbeat interval value 501 is line 511, so the distance between central interbeat interval value 501 and atrial line 511 is maintained. For the second RR-baseline, the nearest atrial line to central interbeat interval value 502 is line 512, so the distance between central interbeat interval value 502 and atrial line 512 is maintained. Similarly, the distance between each central interbeat interval value, represented by a dot in FIG. 5, and the atrial lines 511, 512, 513 is determined, and the smallest distance, i.e. the distance to the nearest atrial line, is maintained.

For each atrial rate out of the subset of atrial rates, an average distance of the RR-baseline central interbeat interval values to the nearest atrial lines is determined according to a distance criterion in step 107 of FIG. 1. The distance criterion may for instance be a mean square distance across the RR-baselines. The distance may also be a weighted mean square distance wherein the weights correspond to the length of the RR-baselines. In other words, longer RR-baselines may get a higher weight or importance in the distance criterion. The skilled person will appreciate that other distance criteria may be considered to determine an average distance from RR-baseline central distance interval values to the nearest atrial line for each atrial rate, all embraced within the invention.

In step 108 of FIG. 1, the PPG processing device selects the atrial rate for which the smallest average distance between RR-baseline central distance interval values and the nearest atrial lines has been determined according to steps 106 and 107. In the example illustrated by FIG. 2-5, the atrial rate of 188 bmp, illustrated by FIG. 5, has the smallest average distance.

According to step 109 of FIG. 1, the PPG processing device compares the smallest average distance to a predefined threshold. When the smallest mean distance stays below this predefined threshold, the person is classified as an atrial flutter patient.

In the above-described embodiment, it is assumed that a flutter heart rhythm contains patterns that comprise consecutive RRs or interbeat intervals with the same value, forming the so-called RR-baselines (typically short time intervals with very regular heart rate). A second assumption is that the interbeat intervals of RR-baselines fall on lines that are all integer fractions of a common base atrial rate, and where the AR/VR ratio or so-called AV conduction ratio is 2:1, 3:1 or 4:1.

Figure 6:
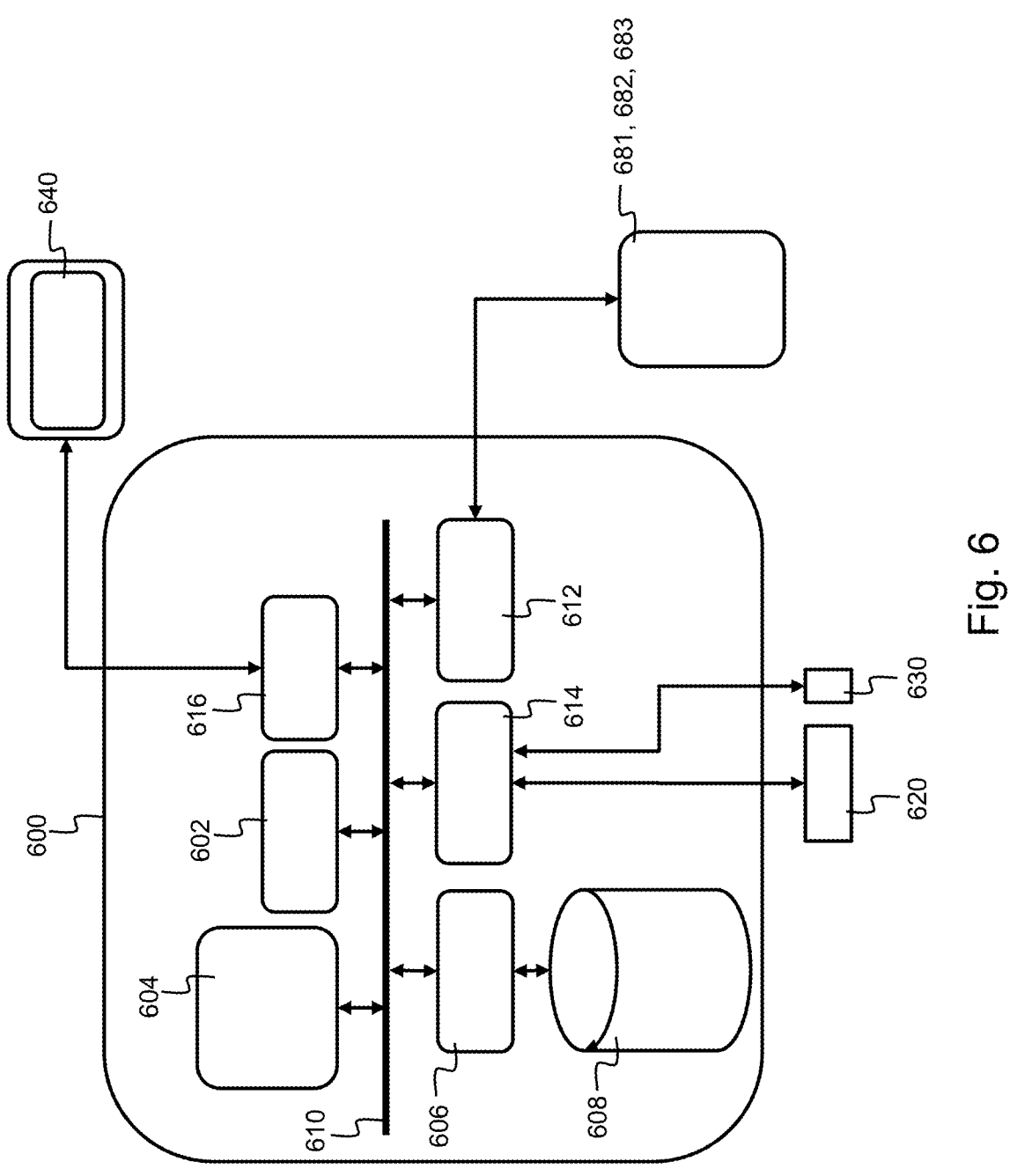
FIG. 6 illustrates a suitable computing system 600 for realizing embodiments of the PPG processing device according to the present invention.

FIG. 6 shows a suitable computing system 600 according to an embodiment of the invention. Computing system 600 is suitable for implementing embodiments of the PPG processing device in line with the present invention. Computing system 600 may in general be formed as a suitable general-purpose computer and comprise a bus 610, a processor 602, a local memory 604, one or more optional input interfaces 614, one or more optional output interfaces 616, a communication interface 612, a storage element interface 606 and one or more storage element 608. Bus 610 may comprise one or more conductors that permit communication among the components of the computing system 600. Processor 602 may include any type of conventional processor or microprocessor that interprets and executes programming instructions. Local memory 604 may include a random access memory (RAM) or another type of dynamic storage device that stores information and instructions for execution by processor 602 and/or a read only memory (ROM) or another type of static storage device that stores static information and instructions for use by processor 602. Input interface 614 may comprise one or more conventional mechanism that permit an operator or user to input information to the computing device 600, such as a keyboard 620, a mouse 630, a pen, voice recognition and/or biometric mechanisms, a camera, etc. Output interface 616 may comprise one or more conventional mechanisms that output information to the operator or user, such as a display 640, etc. Communication interface 612 may comprise any transceiver-like mechanism such as for example one or more Ethernet interfaces that enables computing system 600 to communicate with other devices and/or systems, for example with other computing devices 681, 682, 683. The communication interface 612 of computing system 600 may be connected to such another computing system by means of a local area network (LAN) or a wide area network (WAN) such as for example the internet. Storage element interface 606 may comprise a storage interface such as for example a Serial Advanced Technology Attachment (SATA) interface or a Small Computer System Interface (SCSI) for connecting bus 610 to one or more storage elements 608, such as one or more local disks, for example SATA disk drives, and control the reading and writing of data to and/or from these storage elements 608. Although the storage elements 608 above is described as a local disk, in general any other suitable computer-readable media such as a removable magnetic disk, optical storage media such as a CD or DVD-ROM disk, solid state drives, flash memory cards, . . . could be used. It is noticed that the entire method according to the present invention can be executed centralized, e.g. on a server in a management centre or in a cloud system, or it can be partially executed on a remote electronic device, e.g. worn by the user, and partially on a central server. Computing system 600 could thus correspond to the processing system available centrally or the processing system available in the electronic device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A photoplethysmography signal processing device, abbreviated as PPG signal processing device, configured to detect atrial flutter, said PPG signal processing device comprising at least one processor and at least one memory including computer program code, the at least one memory and the computer program code configured to, with the at least one processor, cause the PPG signal processing device to:

obtain at least one photoplethysmography signal (200), abbreviated as PPG signal, for a human or animal;

detect heartbeats in said at least one PPG signal;

determine interbeat intervals for pairs of consecutive heartbeats in said at least one PPG signal;

detect interbeat interval baselines, each interbeat interval baseline corresponding to a plurality of consecutive interbeat intervals that are substantially constant;

determine respective average interbeat interval values for respective ones of said interbeat interval baselines; and detect arterial flutter by detecting the existence of a relationship between said average interbeat interval values as follows:

determine respective distances between said average interbeat interval values of said interbeat interval baselines and nearest atrial lines for a subset of atrial rates, wherein said subset of atrial rates comprises integer beat per minute values between a lower bound and an upper bound and wherein atrial lines correspond to integer parts of said atrial rates;

determine for each atrial rate in said subset of atrial rates an average distance between said average interbeat interval values and nearest atrial lines for said atrial rate;

select the atrial rate for which said average interbeat interval values have the smallest average distance to the atrial lines; and detect atrial flutter if said smallest average distance is smaller than a predetermined threshold distance.

2. A PPG signal processing device according to claim 1, wherein said average distance corresponds to a weighted square distance wherein the length or duration of an interbeat interval baseline serves as respective weight for the square distance between said average interbeat interval value of said interbeat interval baseline and a nearest atrial line in said average distance.

3. A PPG signal processing device according to claim 1, wherein said atrial lines for an atrial rate out of said subset of atrial rates correspond to half of said atrial rate, a third of said atrial rate, and a fourth of said atrial rate.

4. A PPG signal processing device according to claim 1, wherein said subset of atrial rates comprises all integer rates between a lower bound and an upper bound.

5. A PPG signal processing device according to claim 1, wherein an average interbeat interval value for an interbeat interval baseline corresponds to one of the following:

the mean value of interbeat interval values that belong to said interbeat interval baseline;

the median value of interbeat interval values that belong to said interbeat interval baseline;

the modus value of interbeat interval values that belong to said interbeat interval baseline; or the mid-range value of interbeat interval values that belong to said interbeat interval baseline.

6. A PPG signal processing device according to claim 1, further comprising means to configure a minimum amount for said plurality of consecutive interbeat intervals that forms an interbeat interval baseline.

7. A PPG signal processing device according to claim 1, further comprising means to configure said predefined tolerance value.

8. A computer-implemented method for processing a photoplethysmography signal, abbreviated as PPG signal, to detect atrial flutter, said method comprising:

obtaining at least one photoplethysmography signal, abbreviated as PPG signal, for a human or animal;

detecting heartbeats in said at least one PPG signal;

determining interbeat intervals for pairs of consecutive heartbeats in said at least one PPG signal;

detecting interbeat interval baselines, each interbeat interval baseline corresponding to a plurality of consecutive interbeat intervals that are substantially constant;

determining respective average interbeat interval values for respective ones of said interbeat interval baselines; and detecting arterial flutter by detecting the existence of a relationship between said average interbeat interval values as follows:

determining respective distances between said average interbeat interval values of said interbeat interval baselines and nearest atrial lines for a subset of atrial rates, wherein said subset of atrial rates comprises integer beat per minute values between a lower bound and an upper bound and wherein atrial lines correspond to integer parts of said atrial rate;

determining for each atrial rate in said subset of atrial rates an average distance between said average interbeat interval values and nearest atrial lines for said atrial rate;

selecting the atrial rate for which said average interbeat interval values have the smallest average distance to the atrial lines; and detecting atrial flutter if said smallest average distance is smaller than a predetermined threshold distance.

9. A computer program product comprising computer-executable instructions for performing the method according to claim 8, when the program is run on a computer.

10. A computer readable storage medium comprising:

the computer program product according to claim 9.

* * * * *